US010459227B2

(12) United States Patent
Norrell

(10) Patent No.: US 10,459,227 B2
(45) Date of Patent: Oct. 29, 2019

(54) METHOD OF VISUALLY OUTPUTTING TO A WORKER DURING AN OPERATION A NUMBER OF PARAMETERS PERTAINING TO THE OPERATION, AND ASSOCIATED APPARATUS

(71) Applicant: WESTINGHOUSE ELECTRIC COMPANY LLC, Cranberry Township, PA (US)

(72) Inventor: Michael S. Norrell, Bridgeville, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 0 days.

(21) Appl. No.: 15/963,159

(22) Filed: Apr. 26, 2018

(65) Prior Publication Data
US 2018/0239139 A1 Aug. 23, 2018

Related U.S. Application Data

(63) Continuation-in-part of application No. 15/592,822, filed on May 11, 2017, now Pat. No. 10,007,002, and
(Continued)

(51) Int. Cl.
*G02B 27/01* (2006.01)
*G08B 21/14* (2006.01)
(Continued)

(52) U.S. Cl.
CPC .......... *G02B 27/017* (2013.01); *B23K 9/0956* (2013.01); *B23K 9/1062* (2013.01);
(Continued)

(58) Field of Classification Search
CPC .... B23K 9/0956; B23K 9/173; B23K 37/006; B23K 9/1062; B23K 9/322; G02B 27/017;
(Continued)

(56) References Cited

U.S. PATENT DOCUMENTS 4,642,463 A 2/1987 Thoms
10,055,971 B2 * 8/2018 M R .................. G06F 19/3418
(Continued)

FOREIGN PATENT DOCUMENTS

EP 2515145 10/2012
JP 57179679 5/1982
(Continued)

OTHER PUBLICATIONS

Westinghouse Electric Company LLC, PCT/US2016/017957 International Search Report, dated Jun. 30, 2016, 3 pages.
(Continued)

*Primary Examiner* — Marcus H Taningco
*Assistant Examiner* — Fani Boosalis
(74) *Attorney, Agent, or Firm* — Eckert Seamans Cherin & Mellott, LLC; Brij K. Agarwal

(57) ABSTRACT

A method includes detecting currently existing dose rates while a worker is performing an operation within a Radiologically Controlled Area (RCA) and visually outputting to the worker a dosage rate map of ionizing radiation within the RCA. The visual output can be visually depicted on a display that is worn by the worker during the operation and that is situated in proximity to the worker's eye. Another method of visually outputting to a worker a number of visual indicia that are representative of a number of parameters of an operation performed inside or outside the RCA includes periodically receiving a number of inputs from a number of detectors, employing the inputs to determine values for the parameters, and depicting the number of visible indicia on an electronic visual display that is situated on the worker and that is disposed proximate an eye of the worker.

19 Claims, 8 Drawing Sheets

Related U.S. Application Data a continuation-in-part of application No. 15/043,899, filed on Feb. 15, 2016, now Pat. No. 9,664,796.

(60) Provisional application No. 62/115,939, filed on Feb. 13, 2015, provisional application No. 62/115,939, filed on Feb. 13, 2015.

(51) Int. Cl.

| | |
|---|---|
| *B23K 37/00* | (2006.01) |
| *G01N 33/00* | (2006.01) |
| *B23K 9/095* | (2006.01) |
| *B23K 9/10* | (2006.01) |
| *B23K 9/173* | (2006.01) |
| *B23K 9/32* | (2006.01) |
| *G08B 3/10* | (2006.01) |
| *G08B 25/08* | (2006.01) |
| *G08B 25/10* | (2006.01) |

(52) U.S. Cl.
CPC .............. *B23K 9/173* (2013.01); *B23K 9/322* (2013.01); *B23K 37/006* (2013.01); *G01N 33/0075* (2013.01); *G08B 3/10* (2013.01); *G08B 21/14* (2013.01); *G08B 25/08* (2013.01); *G08B 25/10* (2013.01); *G02B 2027/0141* (2013.01); *G02B 2027/0178* (2013.01); *G02B 2027/0181* (2013.01)

(58) Field of Classification Search
CPC .... G02B 2027/0141; G02B 2027/0178; G02B 2027/0181; G08B 21/14; G08B 25/08; G08B 25/10; G08B 3/10; G01N 33/0075
See application file for complete search history.

(56) References Cited

U.S. PATENT DOCUMENTS

| | | | |
|---|---|---|---|
| 2006/0237648 | A1 | 10/2006 | Bushberg |
| 2007/0120695 | A1* | 5/2007 | Albarado ............. B23K 26/032 340/679 |

FOREIGN PATENT DOCUMENTS

| | | |
|---|---|---|
| JP | 60185186 | 9/1985 |
| JP | 2006-58220 | 3/2006 |
| KR | 20070073666 | 7/2007 |
| WO | 2008051657 | 5/2008 |
| WO | 2014191957 | 12/2014 |

OTHER PUBLICATIONS

Westinghouse Electric Company LLC, EP 16750052.9 Search Report, 10 pages.

* cited by examiner

| TASK | PLANNED DOSE RATE (mR/hr) | ACTUAL DOSE RATE (mR/hr) | PLANNED STEP TIME (hr) | PLANNED STEP TOTAL (hr) | PLANNED DOSE TOTAL (mR) | ACTUAL DOSE TOTAL (mR) | DOSE LIMIT | PLANNED TIME LEFT (hr) | ACTUAL TIME LEFT (hr) | VARIANCE TIME LEFT | TREND VARIANCE TIME LEFT | TREND DOSE TOTAL |
|---|---|---|---|---|---|---|---|---|---|---|---|---|
| 0 | 5 | 5 | 0 | 0 | 0 | 0 | 80 | 16.00 | 16.00 | 0.00 | | |
| 1 | 5 | 6 | 0.1 | 0.1 | 0.5 | 0.72 | | 15.90 | 13.21 | -0.17 | ⇓ | 0.44 |
| | 5 | 7 | 0.1 | 0.2 | 1 | 1.28 | | 15.80 | 11.25 | -0.29 | ⇓ | 0.28 |
| | 5 | 4 | 0.1 | 0.3 | 1.5 | 1.68 | | 15.70 | 19.58 | 0.25 | ⇑ | 0.12 |
| 2 | 15 | 14 | 0.1 | 0.4 | 3 | 2.66 | | 5.18 | 5.52 | 0.08 | ⇑ | -0.11 |
| | 15 | 13 | 0.1 | 0.5 | 4.5 | 3.7 | | 5.03 | 5.87 | 0.17 | ⇑ | -0.18 |
| | 15 | 12 | 0.1 | 0.6 | 6 | 5.02 | | 4.93 | 6.25 | 0.27 | ⇑ | -0.16 |
| | 15 | 16 | 0.1 | 0.7 | 7.5 | 6.78 | | 4.83 | 4.58 | -0.05 | ⇓ | -0.1 |
| | 15 | 16 | 0.1 | 0.8 | 9 | 7.74 | | 4.73 | 4.52 | -0.05 | ⇓ | -0.14 |
| | 15 | 15 | 0.1 | 0.9 | 10.5 | 9.54 | | 4.63 | 4.70 | 0.01 | ⇑ | -0.09 |
| | 15 | 18 | 0.1 | 1 | 12 | 11.34 | | 4.53 | 3.81 | -0.16 | ⇓ | -0.06 |
| | 15 | 12 | 0.1 | 1.1 | 13.5 | 12.54 | | 4.43 | 5.62 | 0.27 | ⇑ | -0.07 |
| | 15 | 11 | 0.1 | 1.2 | 15 | 13.2 | | 4.33 | 6.07 | 0.40 | ⇑ | -0.12 |
| | 15 | 16 | 0.1 | 1.3 | 16.5 | 14.48 | | 4.23 | 4.10 | -0.03 | ⇓ | -0.12 |
| | 15 | 55 | 0.1 | 1.4 | 21.5 | 19.43 | | 1.17 | 1.10 | -0.06 | ⇓ | -0.1 |
| 3 | 50 | 58 | 0.1 | 1.5 | 26.5 | 23.49 | | 1.07 | 0.97 | -0.09 | ⇓ | -0.11 |
| | 50 | 55 | 0.1 | 1.6 | 31.5 | 28.99 | | 0.97 | 0.93 | -0.04 | ⇓ | -0.08 |
| | 50 | 55 | 0.1 | 1.7 | 36.5 | 35.59 | | 0.87 | 0.81 | -0.07 | ⇓ | -0.02 |
| | 50 | 52 | 0.1 | 1.8 | 41.5 | 41.31 | | 0.77 | 0.74 | -0.03 | ⇓ | -0 |
| | 50 | 49 | 0.1 | 1.9 | 46.5 | 46.21 | | 0.67 | 0.69 | 0.03 | ⇑ | 0.01 |
| | 50 | 24 | 0.1 | 2 | 51.5 | 49.33 | | 0.57 | 1.28 | 1.24 | ⇑ | -0.04 |
| | 50 | 55 | 0.1 | 2.1 | 56.5 | 54.28 | | 0.47 | 0.47 | -0.01 | ⇓ | -0.04 |
| | 50 | 50 | 0.1 | 2.2 | 61.5 | 59.28 | | 0.37 | 0.41 | 0.12 | ⇑ | -0.04 |
| | 50 | 55 | 0.1 | 2.3 | 66.5 | 66.43 | | 0.27 | 0.25 | -0.09 | ⇓ | 0 |
| 4 | 25 | 25 | 0.1 | 2.4 | 69 | 69.07 | | 0.44 | 0.46 | 0.04 | ⇑ | 0.001 |
| | 25 | 23 | 0.1 | 2.5 | 71.5 | 70.91 | | 0.34 | 0.40 | 0.16 | ⇑ | -0.01 |
| | 25 | 22 | 0.1 | 2.6 | 74 | 72.89 | | 0.24 | 0.32 | 0.35 | ⇑ | -0.01 |
| | 25 | 24 | 0.1 | 2.7 | 76.5 | 74.57 | | 0.14 | 0.23 | 0.62 | ⇑ | -0.03 |
| 5 | 5 | 4 | 0.1 | 2.8 | 77 | 74.97 | | 0.60 | 1.26 | 1.10 | ⇑ | -0.03 |
| | 5 | 5 | 0.1 | 2.9 | 77.5 | 75.42 | | 0.50 | 0.92 | 0.83 | ⇑ | -0.03 |
| | 5 | 3 | 0.1 | 3 | 78 | 75.6 | | 0.40 | 1.47 | 2.67 | ⇑ | -0.03 |

FIG. 3

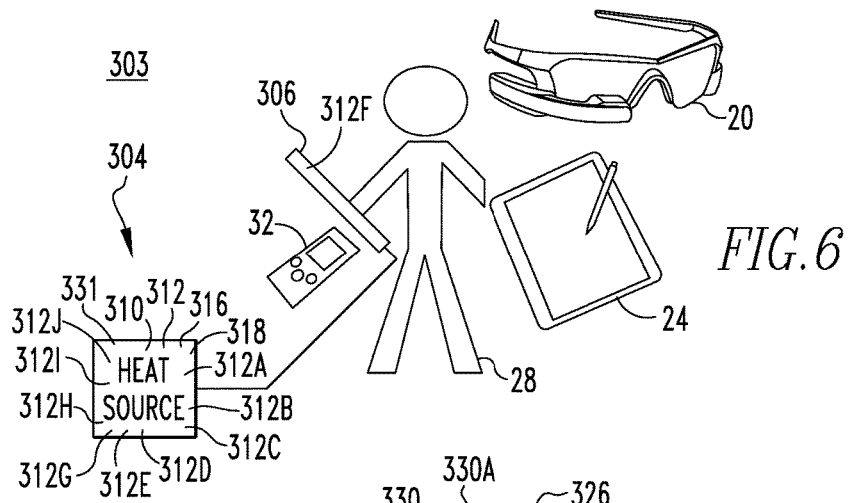
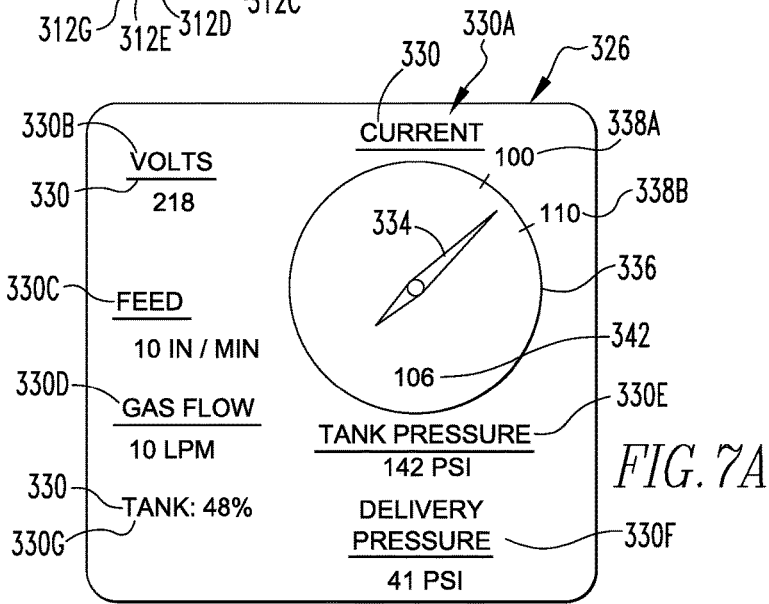
FIG. 6
FIG. 7A
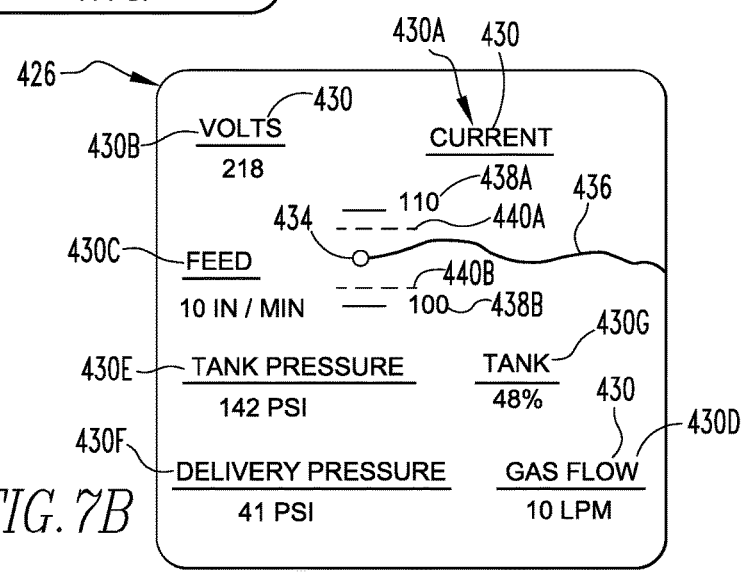
FIG. 7B

METHOD OF VISUALLY OUTPUTTING TO A WORKER DURING AN OPERATION A NUMBER OF PARAMETERS PERTAINING TO THE OPERATION, AND ASSOCIATED APPARATUS

CROSS REFERENCE TO RELATED APPLICATION

The instant application claims priority from U.S. Provisional Patent Application Ser. No. 62/115,939 filed Feb. 13, 2015, from U.S. patent application Ser. No. 15/043,899 filed Feb. 15, 2016, and from U.S. patent application Ser. No. 15/592,822 filed May 11, 2017, the disclosures of which are incorporated herein by reference.

BACKGROUND

1. Field

The disclosed and claimed concept relates generally to operations such as welding operations and, more particularly, to a method of visually outputting a number of parameters to a worker during performance of the operation by outputting a number of visual indicia on an electronic visual display that is situated on the worker and is disposed proximate an eye of the worker.

2. Related Art

As is generally understood in the relevant art, operations such as maintenance operations, repair operations, and the like are necessary or desirable to be performed in a Radiologically Controlled Area (RCA). As is likewise understood in the relevant art, RCAs exist in nuclear power plant facilities, such as within the nuclear containment of such facilities, and in other places. Many such maintenance and other such operations within an RCA must be carried out by human personnel such as plant workers and the like. In such a situation, the worker who is situated inside the RCA is subjected to nuclear radiation, which is generally undesirable, so the worker typically is limited to at most only a certain predetermined amount of nuclear radiation, which is often measured in millirems.

In order to ascertain the number of millirems to which a worker is exposed during an operation within an RCA, it has been known to dispatch a number of personnel to the RCA for the purpose of measuring the various radiation dose rates at the various locations within an RCA where a worker may be expected to go. Such position-based dose rates, i.e., in millirems per hour, are then employed by planning personnel at the facility to plan the maintenance and other operations that are intended to occur within the RCA. The planning personnel consider the various dose rates at the various locations in the RCA and the amount of time that is anticipated for the worker to spend at various locations within the RCA. An estimated dose is estimated based upon the various dose rates that the worker will likely experience over the course of the operation. Various safety factors are built into the calculation in order to ensure that the radiation to which the worker is exposed does not exceed the maximum allowable dose.

While systems of this type have been generally effective for their intended purposes, they have not been without limitation. For instance, the safety factors that are built into the plans for performing the various operations are typically in the form of additional time, whereby the worker typically is removed from the RCA after a limited amount of time in order to ensure that the worker has not been subjected to more than the allowable dose of radiation. This is regardless of whether the maximum allowable dose has actually been received by the worker, and it increases the cost of performing maintenance and other activities in the RCA. Additionally, such planned operations are based only upon the data that was collected prior to the maintenance operation actually being performed, and it is therefore possible that the worker can be overexposed to radiation in excess of the maximum allowable dose despite the safety factors and precautions that are built into the operation. Overexposure of a worker to radiation is extremely costly and it is desirably avoided. Improvements thus would be desirable.

Operations such as maintenance operations, repair operations, and the like can include welding operations that may or may not be performed within the RCA. As is known in the general art, a welding operation typically involves the use of some type of a welding machine that typically employs electricity or combustible gases to produce heat to form a weld. The welding machine typically includes some type of a welding instrument that is manually held by the worker and which actually forms the weld on the workpiece. The welding machine typically also includes some type of a heat source, such as a source of electrical energy or combustible gases to generate the heat that is used by the welding instrument. The welding machine may further include supplies of additional materials that can vary depending upon the welding technology that is employed. For instance, additional materials that are used in certain welding technologies may include a supply of metal, typically in the form of an electrode of some type or a length of wire that is melted to form a part of the weld. Another such additional material is any one or more types of inert gases (e.g., noble gases and the like) that are provided at the location of the weld while it is being formed in order to provide an oxygen-free environment at the location where the weld is being formed.

It is also known that the character of a weld can be based upon a pre-established specification for the weld that must be adhered to in order to ensure that the weld will pass inspection. The weld specification might include specified properties such as the voltage and current that were employed, the pressure of the inert gas that was supplied to the weld, a wire feed rate of the electrode material, and the like without limitation. While the worker who forms the weld can usually adjust a number of settings on a welding machine prior to initiating the weld, there typically exists a possibility that the settings can somehow become changed or that for whatever reason the specification is somehow otherwise unmet, and this often can happen without the knowledge of the worker. Additionally, dangerous conditions can develop in the environment in which the weld is being formed without the worker necessarily knowing of the existence of such dangerous conditions, which is an undesirable situation that is preferably avoided. Improvements thus would be desirable.

SUMMARY

An improved method in accordance with the disclosed and claimed concept includes detecting on an ongoing basis the currently existing dose rates while a worker is performing a maintenance or other operation within the RCA, and visually outputting to the worker or to another person such as a supervisor information that pertains to the ionizing radiation to which the worker is being exposed during the operation. The information that is visually output can include information such as the current dose rate and the overall dose to which the worker has been subjected, but can additionally include information such as the time remaining before which the worker will have been exposed to the maximum allowable dose. Furthermore, it is possible for the visual display to output visual indicia that represent a comparison between the exposure to ionizing radiation that had been planned as a function of time prior to the operation being commenced with the actual exposure to ionizing radiation as the operation is performed. The various visual outputs can be visually depicted on a display that is worn by the worker during the operation and that is situated in proximity to the worker's eye, such as by projecting the visual information onto a lens of a set of glasses worn by the worker. Additionally or alternatively, the same information can be output on a visual display that is observed by a person outside the RCA, such as a supervisor. Additionally, the position of the worker within the RCA, such as in the form of x,y coordinates or x,y,z coordinates within the RCA, can be stored in conjunction with the measured dose rate at such location as detected by a dosimeter worn by the worker, potentially also with a time stamp. These data can be recorded in a database that is described in greater detail below. The data in the database can then be employed to generate a dosage rate map of the RCA that shows the various dose rates at various locations within the RCA and that can be visually output for viewing by the worker, such as on the aforementioned set of glasses, and can additionally or alternatively be output for viewing by a supervisor or other personnel outside the RCA. Additionally or alternatively, an improved method of visually outputting to a worker a number of visual indicia that are representative of a number of parameters of an operation includes periodically receiving a number of inputs from a number of detectors, employing the inputs to determine values for the parameters, and depicting the number of visible indicia on an electronic visual display that is situated on the worker and that is disposed proximate an eye of the worker.

Accordingly, an aspect of the disclosed and claimed concept is to provide an improved method of visually outputting indicia that include information pertaining to the actual dose of ionizing radiation to which the worker has been exposed and that is updated on a continual basis.

Another aspect of the disclosed and claimed concept is to provide visible output that includes indicia that are representative of the time remaining before a worker will be exposed to a maximum allowable dose and that can include other indicia that are representative of a comparison between a planned exposure to ionizing radiation compared with an actual exposure to ionizing radiation.

Another aspect of the disclosed and claimed concept is to visually output a dosage rate map that depicts the various dosage rates of various locations within an RCA for viewing by a worker performing an operation and/or by another person situated outside the RCA.

Another aspect of the disclosed and claimed concept is to provide to a worker visual information pertaining to an operation that is being performed by the worker and to visually depict such information on a visual display device that is worn by the worker and that is disposed proximate the worker's eye.

Another aspect of the disclosed and claimed concept is to provide to a worker who is performing a welding operation or other operation a number of visible indicia that pertain to the operation and that are displayed on a visual display device that is worn by the worker and that is disposed proximate the worker's eye.

Another aspect of the disclosed and claimed concept is to provide to a worker visible indicia that are continually updated to reflect the continuing updated parameters that pertain to the operation.

Another aspect of the disclosed and claimed concept is to enable the worker to select a particular visual format for the display of the visible indicia.

Another aspect of the disclosed and claimed concept is to provide as a part of the visible indicia one or more of the parameters that pertain to the operation and that are output in such a fashion as to enable the worker to be advised of the values of the parameters prior to the parameters meeting or exceeding the limits of a pre-established specification of the operation.

Another aspect of the disclosed and claimed concept is to bring to the attention of the worker any of a number of environmental parameters that may develop in the environment in which the operation is being performed and that may be dangerous to the worker.

Accordingly, an aspect of the disclosed and claimed concept is to provide an improved method of providing to a worker during an operation wherein the worker is situated within a Radiologically Controlled Area (RCA) continually updated information pertaining to the operation, the method can be generally stated as including detecting a number of measured dose rates at a number of times during the operation, each measured dose rate of the number of measured dose rates being representative of a rate at which the worker is exposed to ionizing radiation at a corresponding time of the number of times, periodically determining, based at least in part upon the number of measured dose rates, a measured accumulated dose at each time of the number of times that is representative of the accumulated exposure of the worker to ionizing radiation since the beginning of the operation, for each time of the number of times: subtracting the corresponding measured accumulated dose from an allowable maximum dose to determine a corresponding actual available dose that is representative of a corresponding additional accumulation of exposure of the worker to ionizing radiation that is permissible during the operation, and determining, based at least in part upon the corresponding actual available dose and a measured dose rate from among the number of measured dose rates, a corresponding actual time remaining until the worker will have been exposed to the allowable maximum dose, and outputting at one or more times of the number of times on a visual display a visible output that includes indicia which is representative, at least in part, of the actual time remaining.

Another aspect of the disclosed and claimed concept is to provide an improved method of visually outputting a set of continually updated data pertaining to a number of dose rates within a Radiologically Controlled Area (RCA) during an operation wherein a worker is situated within an interior region of the RCA. The method can be generally stated as including, for each dosimeter of a number of dosimeters situated within the RCA, periodically detecting from the dosimeter a measured dose rate that is representative of a rate at which the dosimeter is exposed to ionizing radiation, detecting a position within the RCA where the dosimeter is situated when the measured dose rate is detected, and storing in a storage as a part of a data record a data entry that comprises at least the measured dose rate and the position. The method can be further stated as including employing the data record to determine a number of most current dose rates, each most current dose rate of the number of most current dose rates being associated with a corresponding location from among a number of locations within the RCA, the most current dose rate being representative of a rate at which an object situated at the corresponding location would be exposed to ionizing radiation, and outputting on a visual display a visible output that includes a number of visual objects, at least some of visual objects of the number of visual objects each being representative, at least in part, of a most current dose rate of the number of most current dose rates and the corresponding location.

Another aspect of the disclosed and claimed concept is to provide an improved method of visually outputting to a worker during the performance of an operation that is being performed at least in part by the worker a number of visible indicia that are continually updated and that are representative of a number of parameters that pertain to the operation. The method can be generally stated as including periodically receiving a number of inputs from a number of detectors, periodically employing at least some of the inputs of the number of inputs to determine a value for each of at least a subset of parameters of the number of parameters, and depicting the number of visible indicia on an electronic visual display that is situated on the worker and is disposed proximate an eye of the worker, the number of visible indicia being representative of the value that corresponds with each parameter of at least some of the parameters of the at least subset.

Another aspect of the disclosed and claimed concept is to provide an improved welding apparatus structured to be usable by a worker to perform a welding operation. The welding apparatus can be generally stated as including a welding instrument structured to be manually held by the worker, a heat source connected with the welding instrument, a number of detectors, each detector of the number of detectors being structured to detect a property of at least one of the welding instrument, the heat source, and an environment in which the welding apparatus is situated, a processor apparatus connected with the number of instruments and that can be generally stated as including a processor and a storage, an electronic visual display that is structured to be situated on the worker and to be disposed proximate an eye of the worker, the electronic visual display being structured to visually output to the worker during the performance of the operation a number of visible indicia that are continually updated and that are representative of a number of parameters that pertain to the operation, the storage having stored therein a number of routines which, when executed on the processor, cause the processor apparatus to perform a number of operations that can be generally stated as including periodically receiving a number of inputs from the number of detectors, periodically employing at least some of the inputs of the number of inputs to determine a value for each of at least a subset of parameters of the number of parameters, and depicting the number of visible indicia on the electronic visual display.

BRIEF DESCRIPTION OF THE DRAWINGS

A further understanding of the disclosed and claimed concept can be gained from the following Description when read in conjunction with the accompanying drawings in which:

FIG. 3 is an exemplary chart depicting various calculated results and visual outputs that occur during the improved method;

FIG. 6 is a schematic depiction of an improved welding apparatus in accordance with the disclosed and claimed concept being used by a worker to perform an improved method in accordance with the disclosed and claimed concept;

FIG. 7A, FIG. 7B, FIG. 7C, and FIG. 7D depict various visual outputs that are shown on an electronic visual display that is situated on the worker and that is disposed proximate an eye of the worker;

Similar numerals refer to similar parts throughout the specification.

DESCRIPTION

Figure 1:
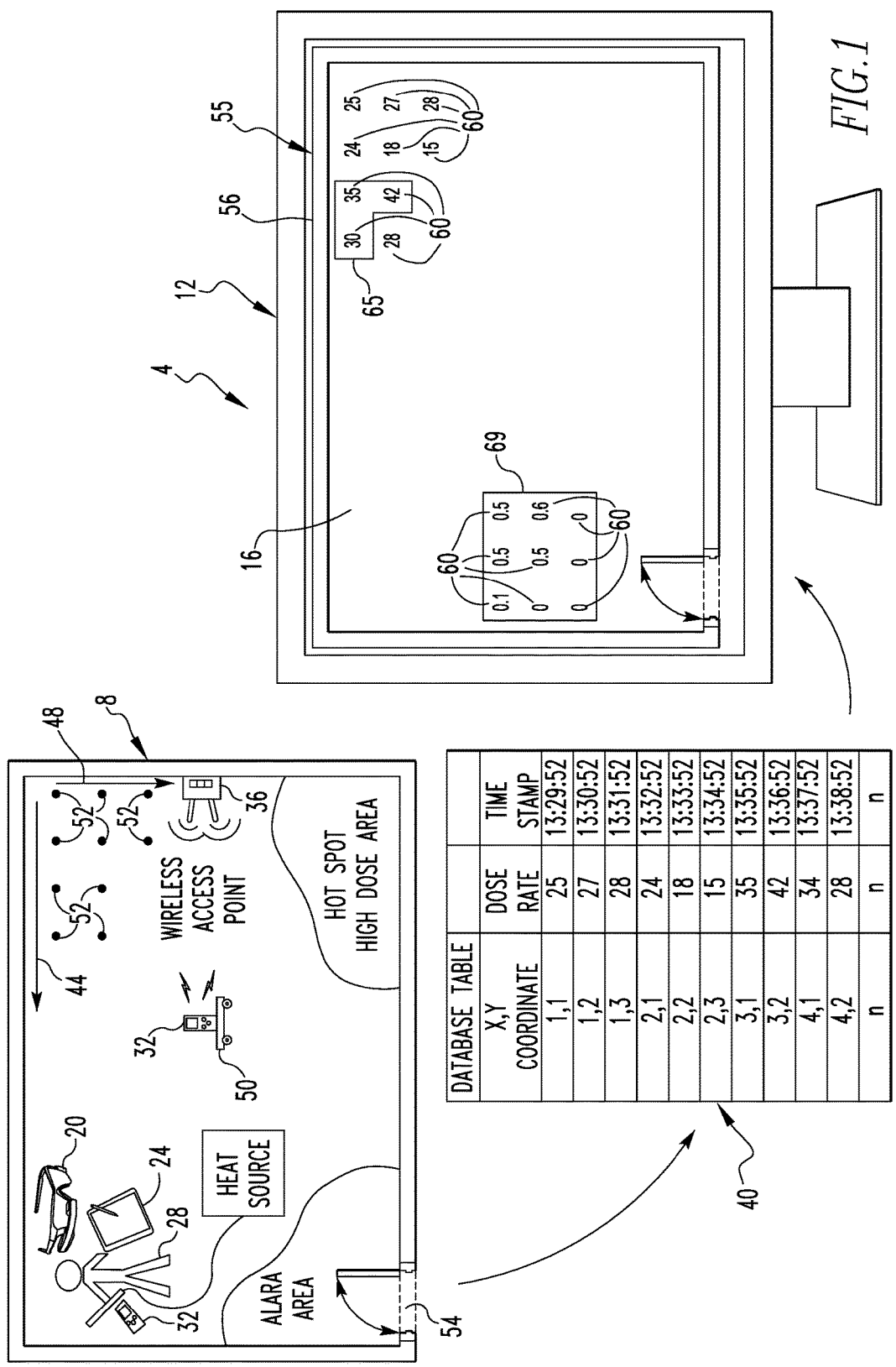
FIG. 1 is a diagrammatic view of a system that is usable to perform an improved method in accordance with the disclosed and claimed concept.

An improved system 4 in accordance with the disclosed and claimed concept is depicted generally in FIG. 1. The system 4 is usable in connection with a radiologically controlled area (RCA) 8 that may be situated within a nuclear containment of a nuclear power plant, by way of example and without limitation. The system 4 includes a computer 12 having a visual display 16 and which is in wireless communication with a set of glasses 20 that can be worn by a worker 28 as well as with a tablet 24 that can be carried by the worker 28. The glasses 20 are a set of smart glasses having a wireless data communication capability and having as its lenses a pair of transparent visual displays on which subject matter can be visually output while the user looks through the transparent lenses in the performing of a maintenance operation or other operation within the RCA 8. The tablet 24 is a computerized device having a visual display and having a wireless data communication capability, and it may alternatively be in the form of a smart phone, a laptop computer, or other personal mobile device, by way of example. The computer 12 additionally includes a storage 140 having a database (DB) 170 stored therein, it being noted that the DB serves as a data record of data that is obtained from inside the RCA 8. The worker 28 additionally carries a portable electronic dosimeter 32 which can include a Geiger counter or other such device that measures the dosage rate of ionizing radiation to which it is subjected.

In the depicted exemplary embodiment, the dosimeter 32 is in wireless communication with the tablet 24 and/or with the glasses 20 and/or with the computer 12. That is, the glasses 20, the tablet 24, and the dosimeter 32 can wirelessly communicate with one another via a Bluetooth wireless connection or other wireless connection. The glasses 20, the tablet 24, and, potentially, the dosimeter 32 can communicate wirelessly with the computer 12 via a number of wireless access points 36 that are in electronic communication with the computer 12. As employed herein, the expression "a number of" and variations thereof shall broadly to any non-zero quantity, including a quantity of one. The number of wireless access points 36 will be situated within the RCA 8 and are configured to not only receive the wireless signals that are being transmitted from the glasses 20, the tablet 24, and the dosimeter 32, but to also communicate wireless signals to such devices. Additionally, the number of wireless access points 36 are able to detect the specific location within the RCA 8 of, for instance, the dosimeter 32 and/or the tablet 24 and/or the glasses 20 at any given time. See the following link regarding Cisco's Wi Fi-Based Location Analytics:
http://www.cisco.com/c/en/us/products/collateral/wireless/mobility-services-engine/white_paper_c11-728970.html For instance, the dosimeter 32 regularly measures the dosage rate of ionizing radiation within the RCA 8, and it communicates this dosage rate information to the tablet 24, by way of example, which communicates such dosage rate data to the wireless access points 36 for communication to the computer 12. Simultaneously therewith, the wireless access points 36 detect the position of the worker 28 along an x axis 44 and a y axis 48, and potentially along a z axis, within the RCA 8 by detecting the location of the dosimeter 32 and/or the tablet 24 and/or the glasses 20. As such, when the dose rate that is detected by the dosimeter 32 is stored in a set of dose rate measured data 40, the set of data 40 additionally includes a position within the RCA 8 where each such dose rate was measured, and further includes a time stamp reflective of the time at which such measurement was taken. The time stamp is generated by a system clock 34. This can be done contemporaneously for any number of dosimeters that may be worn by other personnel within the RCA 8, and this can occur prior to or during the operation in which the worker 28 is involved.

Furthermore, it is noted that the dosimeters 32 need not be solely worn by the worker 28 and the other personnel. For instance one of the dosimeters 32 can be placed upon a movable platform 50 that is movable about the RCA 8. For example, the movable platform could be robotically operable via a wireless connection with the wireless access point 36. Alternatively, the movable platform 50 might have resident thereon its own movement routines and detection system that would enable it to systematically travel over the entire floor, for example, of the RCA 8. As the movable platform 50 moves along the x axis 44 and the y axis 48, the dosimeter 32 will periodically measure the dose rate. With each such dose rate measurement, the measured dose rate and the corresponding location of the dosimeter 32 at the time of such measurement can be communicated as a data entry for inclusion in the database 170, and the data entry can optionally include a time stamp. The corresponding location can be determined using the wireless access point 36, or it can be determined by the movable platform 50 itself. The movable platform 50 can have a lift mechanism that elevates the dosimeter 32 to various heights above the floor of the RCA in order to develop dose rate data along the z axis. In such a situation, the elevation of the dosimeter 32 along the z axis would likely be communicated by the movable platform 50 for storage as part of the data entry for inclusion in the database 170.

It can be seen that FIG. 1 depicts within the RCA 8 a plurality of exemplary locations 52 where dosage rate data was detected and was stored in the set of measured dose rate data 40, along with corresponding x, y coordinates and time stamps. The exemplary locations 52 are depicted in FIG. 1 as being in an exemplary grid pattern, but it is understood that the various locations 52 likely would instead be more irregularly positioned within the RCA 8 because they would be taken while the worker 28 moves through the RCA 8 during the course of performing an operation within the RCA 8. The worker 28 likely would enter through an access port 54 into an area where the dosage rate is As Low As Reasonably Achievable (ALARA) and will begin performing the tasks that are associated with the operation, all the while either moving about from one moment to the next or staying stationary from one moment to the next. The dosimeter 32 may measure dose rates every second, or every fraction of a second, or more or less frequently, depending upon the needs of the particular application.

As will be set forth in greater detail below, the computer 12 advantageously employs the set of measured dose rate data 40 in order to visually depict on the visual display 16 and/or on the glasses 20 a dosage rate map 55 that includes a first visual object 56 that is representative of the RCA 8 and a number of second visual objects 60 that are representative of the various locations within the RCA 8 and that additionally depict the dosage rate at each such location. The dosage rate map 55 can be visibly depicted on the visual display 16, which may itself be situated outside the RCA 8, and it can additionally or alternatively be depicted on the glasses 20. In this regard, it is understood that the glasses 20 are worn by the worker 28 and include one or more lenses that can serve as additional visual displays upon which the dosage rate map 55 and other indicia can be visually depicted. Since the glasses 20 and the lenses themselves are situated in proximity to the eyes of the worker 28, the worker 28 can readily view the dosage rate map 55 and other visual indicia and data such as will be described in greater detail below without having to separately view another device. That is, while such visual indicia can be output on the tablet 24, by way of example, the outputting of such visual indicia on the glasses 20 facilitates the communication of the visual data to the worker 28 without having to separately look at the tablet 24 in order to see such visual indicia.

Advantageously, the visual display 16 and the glasses 20 can additionally visually depict other indicia that are based upon the detected dosage rates as were detected and recorded in the set of measured dose rate data 40. Even more advantageously, such detected dose rate information in the set of measured dose rate data 40 can be compared with what had been the expected exposure to ionizing radiation, and the difference between the expected values and the actual measured values can be represented on the glasses 20 and/or the visual display 16. That is, not only can actual numerical data be output, but more simplistic and easily visually understood indicia can be output to facilitate rapid perception and understanding by the worker 28 and/or another person who might be situated outside the RCA 8 and who may be observing the visual display 16.

Figure 2:
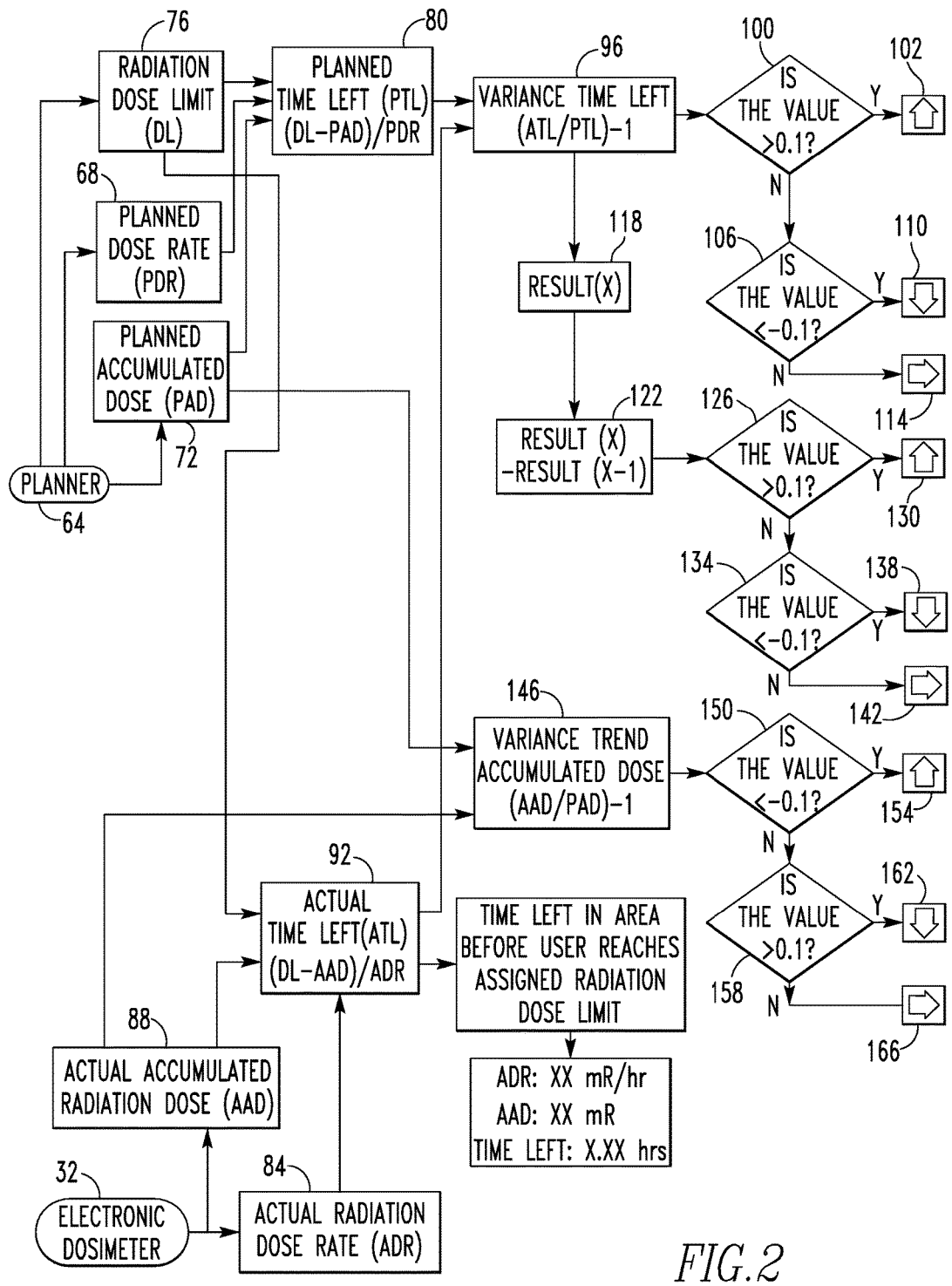
FIG. 2 is a processing diagram depicting certain aspects of the improved method.

By way of example, and as is depicted generally in FIG. 2, the computer 12 may include a planner routine 64 that is executable on the processor of the computer 12 and which can employ whatever dosage rate data currently exists, such as from previous operations that may have been performed by other workers inside the RCA and/or from dosimetry surveys that may have been previously conducted inside the RCA. The planner routine 64 would additionally include data regarding the various tasks that must be performed as part of the operation and the path through the RCA 8 that the worker 28 must follow in order to perform the various tasks. The planner routine 64 would additionally include data regarding the tasks themselves, such as the amount of time that typically would be required of the tasks and would additionally include data regarding the level of experience of the worker 28, such as if the worker was a highly experienced individual who had already performed these same tasks in the past or whether the worker is less experienced with such tasks. The planner routine 64 would then determine a profile as a function of the planned dose rate at each of a plurality of times during the operation, and a planned accumulated dose 72 which would be based upon the planned dose rate 68 and the planned time that the user would spend at the various locations within the RCA 8. All of this information would be compared with a radiation dose limit 76 that represents the maximum dose of ionizing radiation to which the worker 28 is permitted to be exposed. Based upon these data, the planner routine 64 can calculate for each time during the operation a planned time left 80 which is calculated by subtracting the planned accumulated dose 72 from the radiation dose limit and dividing it by the planned dose rate 68 that is expected to be experienced by the worker at the corresponding time. An example of such a set of data is depicted generally in FIG. 3. Each row in FIG. 3 depicts an exemplary six minute period during the operation, which is a time period equal to one-tenth of an hour. The planned accumulated dose 72 is calculated by multiplying the planned dose rate 68 by the relevant period of time that the worker 28 is expected to be exposed to that planned dose rate 68, and such values are accumulated over the course of the operation.

Additionally, the dosimeter 32 detects an actual radiation dose rate 84, and such dose rate data and corresponding position data and time stamps as are depicted in FIG. 1 are saved. The actual radiation dose rate 84 is effectively multiplied by the amount of time that the worker 28 experiences such actual radiation dose rate 84, and such exposure is accumulated to determine an accumulated radiation dose 88. The computer 12, having received the actual radiation dose rate 84 can calculate the actual accumulated radiation dose rate 88 and can further calculate from such data an actual time left 92. The actual time left can be calculated by subtracting the radiation dose limit 76 from the actual accumulated radiation dose and dividing the result by the actual radiation dose rate 84 at any given time. It is noted that the planned time left 80 and the actual time left 92 can be output numerically as a period of time which, in FIG. 3, is measured in hours. Again, such period of time can be depicted on an ongoing and constantly updated basis on the glasses 20 or on the visual display 16 or on both. Since the data is numerical in nature, the worker 28 will need to read the digits and mentally process the digits in order to understand the content of the visual output.

By advantageously employing and providing both actual data via the dosimeter 32 and planned data via the planner routine 64, additional useful information can be developed and visually depicted as visual indicia on the glasses 20 and/or the visual display 16. For example, a variance time left 96 can be calculated by dividing the actual time left by the planned time left and subtracting one therefrom. If the resultant value is greater than 0.1, by way of example, as at 100, a visual indicium 102 such as an upward pointing arrow can be output on the glasses 20 and/or the visual display 16 to indicate that the variance time left trend at any given moment is favorable. On the other hand, if the value is determined, as at 106, to be less than −0.1, an alternative visual indicium 110 that depicts an exemplary downward pointing arrow could be visually output on the glasses 20 and/or the visual display 16 to represent that the variance time left trend is unfavorable. Still alternatively, if the variance time left determined at 96 is neither greater than 0.1 nor less than −0.1, a further alternative indicium 114 can be visually output on the glasses 20 and/or the visual display 16 to represent that the variance time left trend is essentially on track.

While the variance time left trend that is determined at 96 is in the nature of a trend rather than an instantaneous value, it is noted that the set of measured dose rate 40 can be further manipulated, as at 118 and 122. More specifically, the variance time left that is determined at 96 can have subtracted therefrom the immediately prior variance time left value to provide more of an instantaneous determination of variance time left. For instance, if the difference between any given variance time left and the immediately preceding variance time left is greater than 0.1, another visual indicium 130 can be output on the glasses 20 and/or the visual display 16 to indicate that the instantaneous variable time left is favorable by depicting an upward pointing arrow. Alternatively, if the difference is determined at 134 to be less than −0.1, the instantaneous value might result in the outputting of another visual indicium 138 that is represented by a downward pointing arrow, which would suggest that the instantaneous difference is unfavorable, meaning that the variance time left had just become unfavorable. Still alternatively, if it is determined at 134 that the difference determined at 118 and 122 is not less than −0.1, a further visual indicium 142 could be output on the glasses 20 and/or the visual display 16 in the form of a horizontal arrow which would suggest that the instantaneous value difference is on track.

It is understood that the visual indicia 102, 110, and 114 reflect a trend in the variance time left. In contrast, the visual indicia 130, 138, and 142 are directed more toward an instantaneous value for the variance time left rather than a trend. As such, the instantaneous variance time left 122 and the trend variance 96 can be completely different from one another.

It is also possible to determine, as at 146, a variance trend in the accumulated dose, which is calculated by dividing the actual accumulated radiation dose 88 by the planned accumulated dose 72 and subtracting one therefrom. If the resultant value is determined, as at 150, to be less than −0.1, an additional visual indicium 154 which is depicted as an exemplary upward pointing arrow can be output on the glasses 20 and/or the visual display 16, indicating that the variance trend in accumulated dose is favorable. On the other hand, it may be determined, as at 158, that the variance trend accumulated dose is greater than 0.1, in which case an alternative visual indicium 162 can be output on the glasses 20 and/or the visual display 16, indicating that the variance trend in accumulated dose 146 is unfavorable. Still alternatively, if it is determined at 158 that the variance trend is not greater than 0.1, a further alternative visual indicium 166 can be output on the glasses 20 and/or the visual display 16 in the form of an exemplary horizontal arrow, which represents that the variance trend accumulated dose 146 is on track.

It is noted that the variance time left trend indicia 102, 110, and 114 are alternatives of one another and only one of such indicia would be visually output at any given time. Likewise, the visual indicia 130, 138, and 142 are alternatives of one another, and only one of which would be output at any given time. Furthermore, the visual indicia 154, 162, and 166 are alternatives of one another, and only one of which would be output at any given time. It is noted, however, that whichever of the visual indicia 130, 138, and 142 is displayed would be output in addition to whichever of the indicia 102, 110, and 114 is displayed and whichever of the indicia 154, 162, and 166 is displayed. As such, the glasses 20 and/or the visual display 16 would include one of the indicia 102, 110, and 114 representative of the variance time left trend in addition to one of the indicia 130, 138, and 142 representative of the instantaneous variance time left and one of the indicia 154, 162, and 166 that is representative of the variance trend in accumulated dose.

It thus can be seen that the glasses 20 and/or the visual display 16 can not only output the planned time left 80 and an actual time left 92, both in numerical form, the glasses 20 and/or the visual display 16 can additionally include visual depictions of the variance time left trend, the instantaneous variance time left, and the variance trend accumulated dose. The latter three values would be depicted in easily understood forms, such as the aforementioned upward-pointing arrows, downward-pointing arrows, and horizontal arrows, or other such indicia, and may additionally or alternatively include color such as green, red, yellow, and the like to indicate favorable, unfavorable, and on-track values. Other variations will be apparent.

Figure 4:
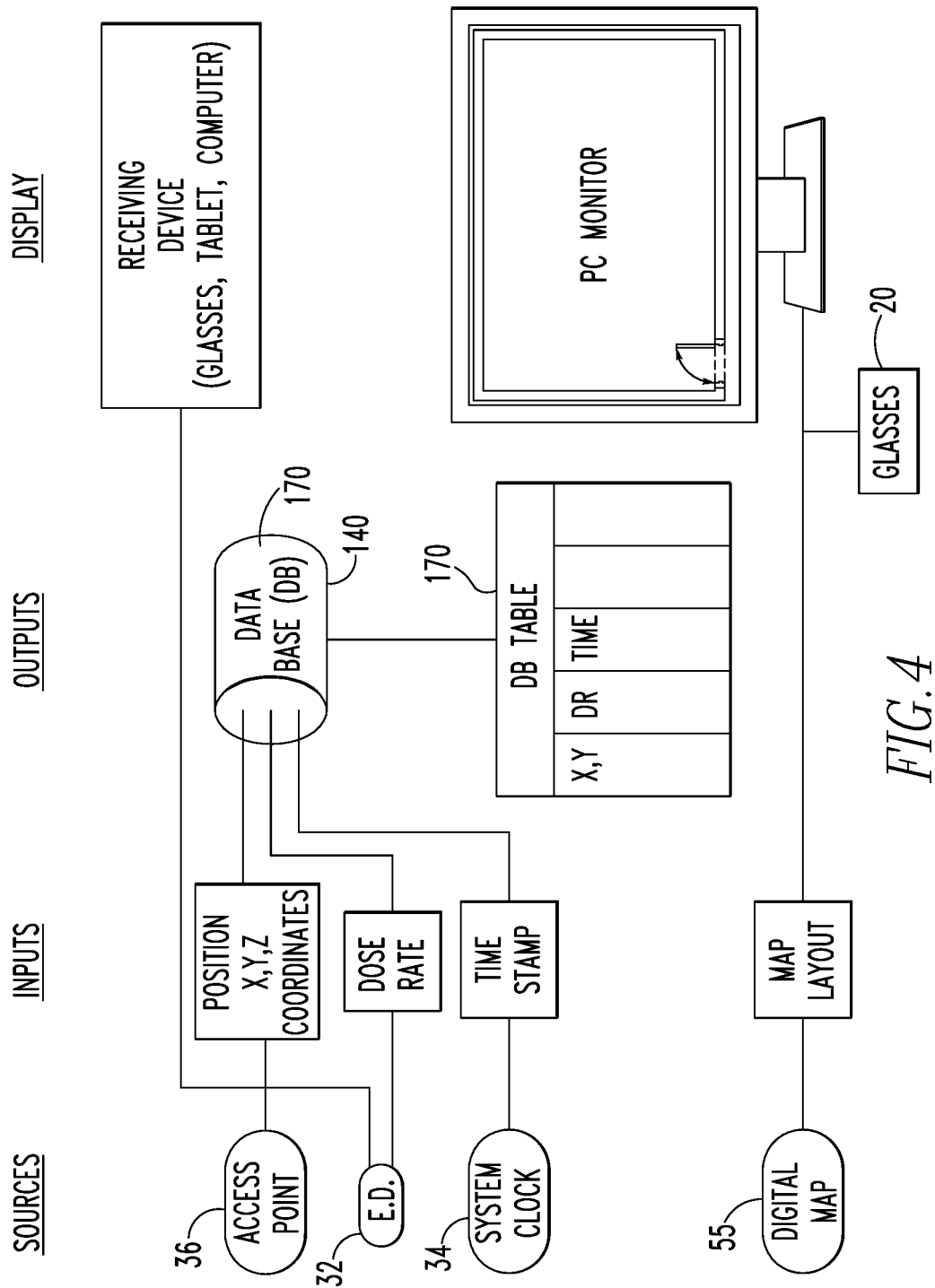
FIG. 4 is a diagram depicting the development of a set of dose rate and position data that is usable to create a dosage rate map such as is depicted in FIG. 1.

FIG. 4 depicts in diagrammatic form the various data sources that generate data which together are stored as the set of measured dose rate data 40 in the database 170 which can be understood to be approximately in the form of a table that includes a location within the RCA 8 in the form of x, y coordinates, a dose rate designated as "DR" and which is the dose rate that was detected at such location, and a "TIME" value which is the time stamp when the dose rate was detected at such location. The various data values are recorded on a continuous basis, and the system can include a loop to delete duplicate values that might be recorded when the worker 28 is stationary, by way of example.

Not only can the data values and the visual indicia that are depicted in FIG. 2 be visually output on the glasses 20 and/or the visual display 16, the set of measured dose rate data 40 can be employed to generate and output the dosage rate map 55 that is depicted in FIG. 1 as being output on the visual display 16. It is expressly noted that the dosage rate map 55 can additionally or alternatively be output on the glasses 20 for use by the worker 28.

As can be seen in FIG. 1, the first visual object 56 is a schematic depiction of the RCA 8. The second visual objects 60 are situated with respect to the first visual object 56 in a fashion that represents the arrangement of the various locations within the RCA 8 where the various dosage measurements were recorded. The second visual objects 60 additionally depict the dosage rate that was recorded. In the depicted exemplary embodiment, these dosage rates are depicted by the second visual objects 60 in a numerical fashion, meaning that the second visual objects 60 each include an indicium in the form of at least a first numeral, but it is understood that the data could alternatively or additionally be conveyed in terms of color, and the like to otherwise depict the dosage rate data. The dose rate data may be taken directly from the set of measured dose rate data 40 or it could be averaged in any of a wide variety of fashions or could be otherwise processed. Still alternatively, the values could be normalized if appropriate. Furthermore, it is understood that the dose rate that is output on the visual display 16 is going to be the most current dose rate that is available, meaning that it reflects the most recent dose rate measurement that has been taken in a given area within the RCA 8. For example, the displayed dose rate in the vicinity where the worker 28 is situated is likely to be accurate and correct, i.e., current, due to repeated dose rate measurements by the dosimeter 32. On the other hand, only a single dose rate may have been recorded for other locations within the RCA 8, and the single dose rate may have been recorded at some time in the past. The single dose rate will still be output if it is the most current dose rate that is available within the set of measured dose rate data 40. In this regard, it is understood that the set of measured dose rate data 40 is a data record that is being continually updated with each additional stored data entry in the form of a new measurement of a dose rate from the dosimeter 32 or another such dosimeter, a corresponding location where the dose rate was measured, and a time stamp of when the dose rate was measured. Whatever data are the most current are used to generate the second visual objects 60. Only a representative number of second visual objects 60 are depicted in FIG. 1, and it is understood that probably many more such second visual objects 60 could be output on the glasses 20 and/or the visual display 16 as the set of measured dose rate data 40 is developed on an ongoing basis over a period of time.

Figure 5:
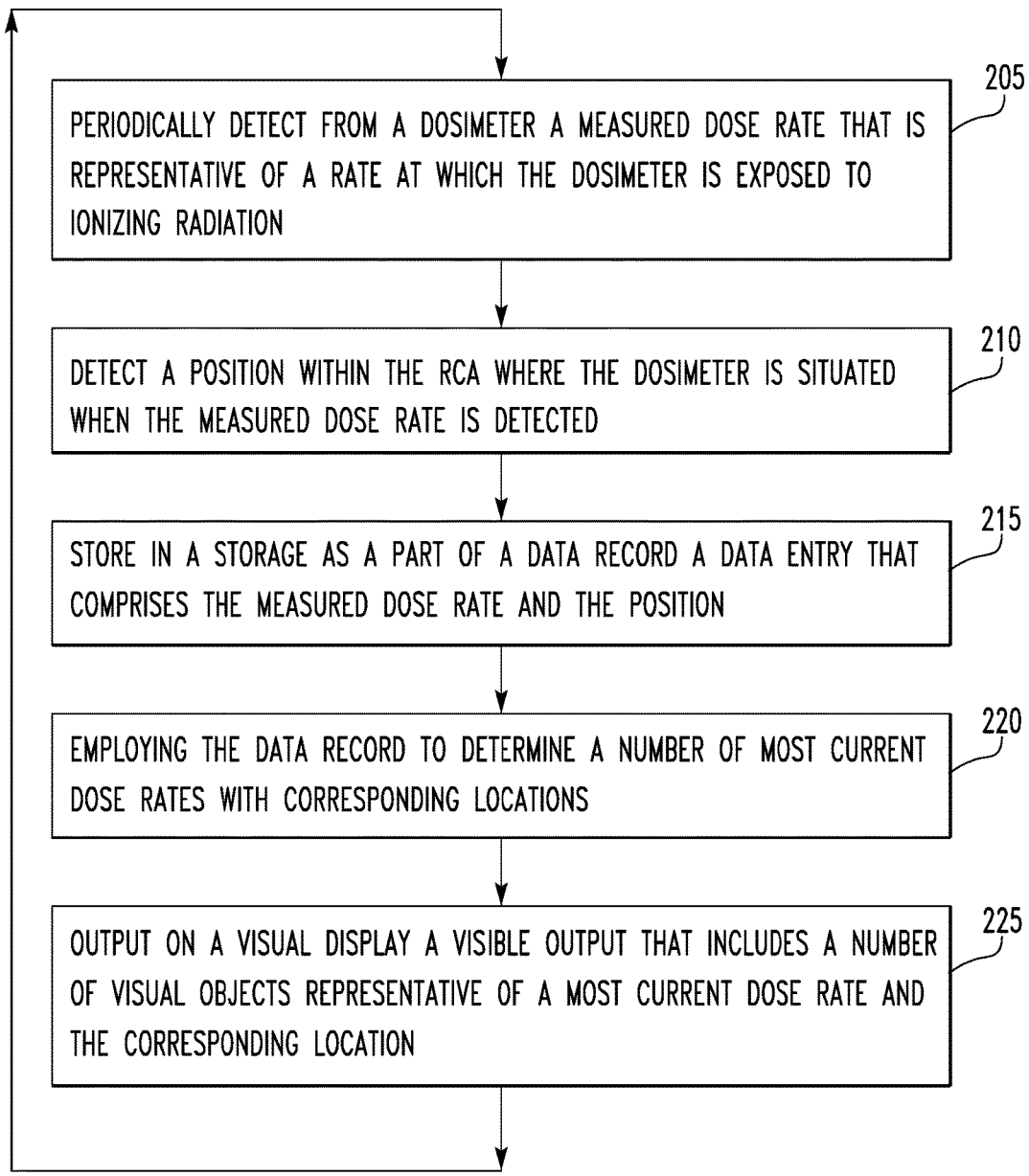
FIG. 5 depicts a flowchart showing certain aspect of an improved method in accordance with the disclosed and claimed concept.

FIG. 5 depicts a flowchart that demonstrates certain aspects of an improved method in accordance with the disclosed and claimed concept. As noted above, the dosimeter 32 can be positioned on the worker 28 and thereby caused to move with the worker 28 from one position to another within the RCA 8 as the worker 28 takes steps necessary to perform the maintenance operation or other operation therein. Any number of other dosimeters 32 can likewise be situated in the RCA 8, such as if they are placed on other workers or if they are situated stationary at one position or another within the RCA 8, etc. For any one or more of the dosimeters 32 within the RCA 8, the method begins, as at 205, with periodically detecting from the dosimeter 32 a measured dose rate that is representative of a rate at which the dosimeter 32 is exposed to ionizing radiation.

Processing continues, as at 210, with the detecting of a position within the RCA 8 where the dosimeter 32 was situated when the dose rate measurement was detected. In this regard, it is noted that the expression "position" and variations thereof is intended to refer herein to the x, y, z coordinates within the RCA 8 where the dosimeter 32 was situated when the dose rate was measured. As will be set forth in greater detail below, the expression "location" and variations thereof is intended to refer to the x, y, z coordinates within the RCA 8 for which a dose rate is output on the visual display 16. While the locations may be the same as the positions, they likewise may be different. In this regard, it is expressly noted that the various dosimeters 32 might detect actual dose rates at numerous positions within the RCA, and many such dose rate measurements may be within very close proximity of one another. As such, it may be more visually understandable to the worker 28 to output as the dosage rate map 55 a set of the most current dose rates at regularly spaced-apart positions within the RCA 8, wherein such locations are located on a virtual grid within the RCA 8. In the depicted exemplary embodiment, the virtual grid would virtually define a plurality of three-dimensional rectangular virtual areas within the RCA, and every time a dose rate measurement from a dosimeter 32 is determined to have been measured in any particular virtual area, the detected dose rate is determined to be the most current dose rate in that virtual area. As such, instead of outputting a large number of dose rates that are in close proximity to one another, the dosage rate map 55 will include only a single dose rate as being the most current dose rate for the entire virtual area. The most current dose rate for a virtual area will be determined based upon the dose rates that were detected within the virtual area. For instance, the most current dose rate could be the highest dose rate detected in that virtual area, or it may be based upon an average of the dose rates measured in the virtual area, or it can be based upon any calculation methodology that may be preferred in any particular virtual area for any particular maintenance operation or other operation. Other variations on how this can be accomplished will be apparent and are considered to be within the spirit of the instant disclosure.

As such, in some embodiments of the disclosed and claimed concept, the dosage rate map 55 potentially may include visual objects that are representative of actual positions where actual dose rates were detected within the RCA 8. It is noted, however, that in other embodiments of the disclosed and claimed concept, the actual measured dose rates might be employed to calculate, such as via interpolation, averaging, and the like, a set of calculated dose rates at specific locations within the RCA to create the dosage rate map 55. Either such methodology will result in a set of most current dose rates depicted via the dosage rate map 55.

It is noted that the predetermined locations need not be evenly spaced along a grid, and rather they may be selected on a practical basis. For example, the bottom of a set of stairs may not be associated with an actual dose rate that was measured at the bottom of the stairs, but it may be worthwhile to employ the data from the other locations within the RCA where dose rate data was actually recorded in order to generate and output an estimation (based upon the recorded dose rate data) as to what the dose rate is understood to be at the bottom of the set of stairs. Other examples will be apparent.

Processing then continues, as at 215, where the dose rate and the corresponding position within the RCA 8 where the dose rate was measured are recorded as a data entry in the database 170. In this regard, the data entry might additionally include a time stamp generated by the system clock 34 whereupon the data entry will include the measured dose rate, the corresponding position where the dose rate was detected, and the corresponding time at which the dose rate was detected. While such time stamp is optional, it can be used to determine what are the most current data values that have been recorded, and such time stamps are further useful in order to determine trends in dose rates and the like.

Processing then continues, as at 220, where the data record, i.e., the database 170 that includes the data entries, is employed to determine a number of most current dose rates and corresponding locations. As noted above, the "locations" may refer to places where a dose rate was actually directly measured via a dosimeter 32 or it may refer to a place for which a dose rate is calculated based upon a number of nearby directly measured dose rates. The dose rates that are determined at 220 are most typically going to be based upon the dose rates that are the most current, i.e., that have been detected and recorded more recently than other dose rate data that may have been measured in the same places at earlier times. Since dose rates are unlikely to be simultaneously detected everywhere within the RCA 8, it is understood that some of the dose rate data may be more current than other dose rate data, but as a general matter the dose rates that are determined at 220 for use in the dosage rate map 55 will based upon whatever dose rate data is the most current.

Processing then continues, as at 225, where the computer 12 outputs on the visual display 16 or on the glasses 20 or both a visual output in the form of the dosage rate map 55. The dosage rate map 55 includes a number of visual objects which are each representative of a most current dose rate and a corresponding location. In this regard, the dosage rate map 55 includes the aforementioned first visual object 56 which is in the form of a representation of the RCA 8. The number of second visual objects 60 each include one or more indicia that are representative of a most current dose rate and a corresponding location where the most current dose rate can be said to exist.

In the depicted exemplary embodiment, one indicium possessed by each of the second visual objects 60 is a numeric representation of the current dose rate. Each of the second visual objects 60 further includes as another indium a relative positioning of itself on the visual display 16 relative to the first visual object 56 which indicates the corresponding location in the RCA 8 with which the current dose rate is associated. That is, an exemplary one of the second visual objects 60 depicted in FIG. 1 includes as one indium the digits "25" as being representative of the current dose rate, and such exemplary second visual object 60 further includes as another indicium its being situated at the uppermost right corner of the dosage rate map 55 (which positioning is representative of the current dose rate of "25" being situated in the upper right corner of the interior of the RCA 8 as represented by the first visual object 56). Such dual indicia indicate the current dose rate of "25" and the corresponding location within the RCA 8 where the current dose rate of "25" exists.

In the depicted exemplary embodiment, each of the second visual objects 60 in FIG. 1 includes additional indicia that are further representative of the dose rate. That is, in addition to the indicium of each of the second visual objects 60 to numerically depict the current dose rate, each of the second visual objects 60 includes as another indicium a color that is representative of the dose rate. For instance, the highest dose rates can be depicted in numerals that are red in color, and lower dose rates can be indicated by numerals depicted in other colors different than red. For example, three of the second visual objects 60 depicted in the upper right of the dosage rate map 55 are surrounded by a border 65 and are additionally output in numerals that are red in color. Additionally, the border 65 itself may be red in color or may be another color or may flash or may provide some other visual indicia that bring to the attention of the worker 28 the fact that those three adjacent locations in the RCA 8 (as indicated by the locations at which the second visual objects 60 are situated with respect to the first visual object 56) are at a relatively high dose rate, meaning that any object that is placed at such locations would experience a high dose rate of ionizing radiation.

In contrast, another set of second visual objects 60 are depicted in FIG. 1 as being situated at the lower left of the dosage rate map 55, and each of the second visual objects 60 in such region are formed from numerals that represent that relatively low dose rates exist in such region, which likely would be an ALARA region. Such ALARA region is surrounded by another border 69 that is likewise intended to visually bring itself to the attention of the worker 28. The second visual objects 60 that are situated within the border 69 are themselves, in addition to including numerals that numerically output the current dose rate at such locations, are depicted using numerals that are printed in a color such as blue which is representative of the fact that the dose rates at such locations are relatively low.

In this regard, it can be seen that the color blue that is used to depict the second visual objects 60 within the border 69 is a color that is different than the color red that is used to depict the second visual objects 60 that are within the border 65. Such difference between the color red and the color blue is intended to visually bring to the attention of the worker 28 the fact that two different regions within the RCA 8 are of significantly different dose rates. Colors between the aforementioned exemplary blue and red may be assigned based upon the then most current dose rate of any given location, and such colors may, for example, span the visual light spectrum between blue and red when going from relatively lower dose rates to relatively higher dose rates.

It is noted that such colors may, for instance, be selected based upon predetermined thresholds of dose rate. For example, a dose rate that is represented by numerals 1.0 or lower might be depicted in the color blue whereas dose rates represented by the numerals 30 or higher might be indicated in red. Variations will be apparent. The border 69 itself may likewise be depicted in blue and/or may be flashing in order to further rapidly bring itself to the attention of the user. In this regard, the border 65 may flash at a relatively fast rate, and the border 69 may flash at a relatively slower rate, with such varying flashing rates further being indicative of the dose rate of the locations contained within such borders 65 and 69. Furthermore, shading, crosshatching, and the like may additionally be present within such borders 65 and 69 if that is deemed to be desirable to make it more readily visually apparent to the worker 28.

It is understood that virtually any type of visual element can be used if that visual element is configured to be representative of a most current dose rate to the worker 28. For example, in certain embodiment it is possible that color alone may be employed in order to depict dose rate, or the flash rate of a visual object alone may be representative of a current dose rate (i.e., faster flashing would indicate a higher dose rate and vice-versa).

It is understood that by visually outputting the first and second visual objects 56 and 60 on the visual display 16, a supervisor or technician or other individual could use the dosage rate map 55 to map out an exit path and/or an entrance path for the worker 28 along a path of a minimal dose rates. Moreover, the dosage rate map 55 depicted on the glasses 20 could be observed by the worker 28 and used by the worker 28 to identify a path of reduced dose rate. In this regard, an instantaneous location of the worker 28 potentially could be output as another visual object on the dosage rate map 55 in order to advise the worker 28 where the worker 28 is situated in the RCA 8 at any given time.

It thus can be seen that the system 4 advantageously can output on the glasses 20 and/or the visual display 16 a set of continually updated data represented by any of a variety of visual indicia, either in a numeric format or a symbolic format or in one or more colors, or any combination thereof, and can additionally visually display the dosage rate map 55 thereon. Such visual outputs assist the worker in determining whether the worker 28 needs to exit the RCA 8 or whether the worker 28 has additional time to complete the various tasks of an operation. Such data output on the visual display 16, which may be situated outside the RCA 8, enables a supervisor or other individual to monitor the progress of the worker 28 and to map out the various tasks that the worker 28 is to perform as well as the specific paths to follow within the RCA 8. By providing the data on a continually updated basis, the worker 28 and other personnel are continually updated regarding the dosage rates and time remaining, as well as the instantaneous and trending aspects of such values, as well as other values. The provision of such data makes the most efficient use of the worker's time within the RCA, thereby saving cost and improving performance. Other benefits will be apparent.

An improved welding apparatus 304 is depicted generally in FIG. 6. The welding apparatus 304 is usable by the worker 28 to perform a welding operation either within the RCA 8 or outside of it. While the exemplary apparatus that is being used by the worker 28 to perform an operation is the exemplary welding apparatus 304, it is understood that the teachings herein can be applied to other equipment that is used to perform other operations without departing from the spirit of the instant disclosure. As is indicated in FIG. 6, the worker 28 can continue to carry the dosimeter 32 and the tablet 24 if this is desirable in an environment 303 such as that within which the welding operation is being performed.

The welding apparatus 304 can be said to include a welding instrument 306 and a heat source 310 that are connected together. The welding instrument 306 is configured to be held manually by the worker 28, as is depicted in FIG. 6, and is a device that actually performs the welding operation on a workpiece. For instance, the welding instrument 306 may be a Metal Inert Gas (MIG) gun, and arc welding electrode, an oxyacetylene torch, or the like, it being noted that numerous other welding technologies exist and which could be performed by the welding apparatus 304 depending upon the configuration of the welding instrument 306 and the heat source 310, by way of example. The heat source 310 is a source of heat that performs the welding operation and can be any of a wide variety of pieces of equipment depending upon the welding technology that may be involved. For instance, the heat source 310 may be a source of welding electricity in the form of a welding machine that is connected with an electrical utility, for instance, and which has dials or the like that can set the various parameters of the electrical power that will be provided to the welding instrument 306 during the welding operation, such as settings for current, voltage, type of current (AC or DC), etc., by way of example. Alternatively, the heat source 310 could be a source of one or more combustible welding gases, such as acetylene and oxygen, by way of example. The specific configuration of the welding instrument 306 and the heat source 310 can vary widely depending upon the welding technology that is being employed by the welding apparatus 304.

The welding apparatus 304 further includes a number of detectors 312 and additionally includes a computer 316 that is connected with the detectors 312. The detectors 312 are configured to detect various parameters that pertain to the welding operation that is being performed by the worker 28 in using the welding apparatus 304. As will be set forth in greater detail below, the number of parameters include a number of operational parameters that pertain to the welding operation itself and further include a number of environmental parameters that pertain to the environment 303 in which the welding operation is being performed. The detectors 312 detect properties of the welding apparatus 304 and of the environment 303 and periodically provide inputs to the computer 316 that are representative of the detected properties. The computer 316 then employs certain of the inputs in order to derive values for the various operational and environmental parameters that are intended to be monitored by the computer 316 and the welding apparatus 304.

The welding apparatus 304 further includes an auxiliary supply system 318 that is configured to provide materials and the like that are appropriate to the welding technology that is being employed by the welding apparatus 304. For instance, if the welding apparatus 304 employs MIG technology, the auxiliary supply system 318 would include, for instance, a tank or other supply of inert gas and would also include a spool or other supply of wire that is intended to be melted in forming the weld. The auxiliary supply system 318 can be configured to provide any materials or the like that are needed in order to perform a particular welding operation with the welding apparatus 304.

The welding apparatus 304 is advantageously in wireless communication with the glasses 20 and is operable to cause the glasses 20 to output a number of visual displays that include various visual indicia that are representative of the values of the operational and environmental parameters that are determined by the welding apparatus 304 based upon the properties that are detected by the detectors. The glasses 20 include one or more electronic visual displays that are at least partially translucent. As employed herein, the expression "translucent" shall refer broadly to a property of transmitting visible light therethrough. The glasses 20 are envisioned to be in wireless communication with the welding apparatus 304, but a wired connection therebetween can be employed depending upon the needs of the particular application.

As noted above, the detectors 312 are different configurations that are configured to detect different properties of the welding apparatus 304 and the environment 303. For instance, the detectors 312 can be said to include a voltmeter 312A, an ammeter 312B, a rotation encoder 312C, a tank pressure sensor 312D, a regulated pressure sensor 312E, a delivery pressure sensor 312F, a flow meter 312G, an oxygen detector 312H, a carbon monoxide sensor 312I, and an optical thermographic sensor 312J, which can be collectively or individually referred to herein with the numeral 312. The detectors 312 can include additional detectors or alternative detectors or both without departing from the spirit of the instant disclosure. For instance, the voltmeter 312A measures the voltage of the electrical current that is being provided from the heat source 310 to the welding instrument 306, and the ammeter 312B measures the amount of current that is being provided from the heat source 310 to the welding instrument 306. The rotation encoder 312C is a device that rotates when wire from the wire supply of the auxiliary supply system 318 is delivered to the weld and responsively outputs electrical pulses that are detected by the computer 316. The tank pressure sensor 312D detects the pressure within the gas tank(s) of the auxiliary supply system 318 or the heat source 310 or both. The regulated pressure sensor 312E detects the pressure of gas, after being regulated by a pressure regulator, that is being supplied to the welding instrument 306 from the auxiliary supply system 318 or the heat source 310, or both. The delivery pressure sensor 312F detects the pressure of gas that is being provided at the welding instrument 306. The flow meter 312G measures the flow rate(s) of gases that are being supplied to the welding instrument 306. The aforementioned detectors 312A-G can be said to be configured to detect operational properties of the welding apparatus 304.

The detectors 312H-J can be said to detect environmental properties within the environment 303 where the welding operation is being performed. For instance, the oxygen detector 312H detects an oxygen level in the environment 303. As can be readily understood, a condition within the environment 303 wherein the oxygen level is increased beyond that typically found in the atmosphere (i.e., 20.95% $O_2$) or that is decreased below that which is typically found in the atmosphere is dangerous, and such a condition is desirably brought promptly to the attention of the worker 28. The carbon monoxide sensor 312I detects the existence of carbon monoxide in the environment 303, it being understood that the presence of any meaningful amount of carbon monoxide is a dangerous condition within the environment 303 and is desirably brought promptly to the attention of the worker 28. The optical thermographic sensor 312J is configured to detect the existence of a fire within the environment 303 which, for obvious reasons, is desirably brought promptly to the attention of the worker 28.

All of the detectors 312 in the depicted exemplary embodiment are shown as being situated on the heat source 310 (which includes therein the auxiliary supply system 318) except for the delivery pressure sensor 312F which is depicted as being situated on the welding instrument 306. It is understood, that such schematic positioning is merely exemplary in nature, and it is noted that the various detectors 312 can be situated otherwise without departing from the spirit of the instant disclosure. For instance, the optical thermographic sensor 312J might be mounted elsewhere in order to have a better ability to detect the existence of fire. Numerous variations will be apparent.

As noted above, the various detectors 312 detect properties of the welding apparatus 304 and the environment 303 and provide outputs that are periodically received as inputs by the computer 316 and that are indicative of the detected properties. The computer 316 employs various routines in order to derive from the measured properties a value for each of a variety of parameters of the welding apparatus 304 and the environment 303. Some of the parameters can be directly measured by the detectors 312 whereas other parameters will be derived from the detected properties. For instance, the rotation encoder 312C will output a series of pulses as it rotates when the wire that is being fed from the auxiliary supply system 318 is delivered to the welding instrument 306. The computer 316 has stored therein a routine that detects the pulses from the rotation encoder 312C and converts the detected pulses into a wire feed rate of a certain length of wire per unit time, by way of example. The tank pressure sensor 312D directly measures the pressure within the tank(s) of the heat source 310 or the auxiliary supply system 318, or both, and while such tank pressure is a parameter of the welding apparatus 304 that may desirably be output on the glasses 20, the measured tank pressure can also be employed to derive the amount of the contents that remain in the tank(s), by way of example. Alternatively, the amount of the contents that remain in the tank(s) might be derived from the output signal from the flow meter 312G. Other variations will be apparent.

The welding apparatus 304 is advantageously configured to generate a number of visual displays, such as the visual display 326 that is depicted in FIG. 7A, and to output the visual display on the glasses 20. In the depicted exemplary embodiment, the visual display 326 includes a number of visual indicia 330 that are representative of values of the parameters that have been generated by the computer 316 based upon the inputs to the computer from the detectors 312. The various exemplary visual indicia 330 that are depicted in FIG. 7A include a current indicium 330A, a voltage indicium 330B, a feed rate indicium 330C, a fluid flow rate indicium 330D, a tank pressure indicium 330E, a delivery pressure indicium 330F, and a tank fullness indicium 330G, which may be collectively or individually referred to herein with the numeral 330. The current indicium 330A is of an analog nature in that includes a depiction of a needle 334 that is depicted superimposed on a depiction of a dial 336 that includes a pair of reference values 338A and 338B. The position of the needle 334 with respect to the reference values 338A and 338B visually depicts the amount of current that is being provided from the heat source 310 to the welding instrument 306. The current indicium 330A further includes a numeric output 334 that provides a numeric indication of the current that is being provided from the heat source 310 to the welding instrument 306.

All of the elements in the current indicium 330A, and indeed all of the elements in all of the visual indicia 330 in the depicted exemplary embodiment, are visual objects that are created by the computer 316 and that are output on the glasses 20. The current indicium 330A can be said to include an analog visual indicium inasmuch as it includes the needle 334 situated on the dial 336 in a position in relation to the first and second reference values 338A and 338B whereby the position of the needle 334 visually indicates the amount of current that is being provided by the heat source 310 to the welding instrument 306. The reference values 338A and 338B each include both a graduation mark that is indicated on the perimeter of the dial 336 and a calibration value "100" and "110", respectively, that indicates the numeric value of the corresponding graduation mark. The reference values 338A and 338B may simply be provided in order to indicate in a visual fashion the current that is being supplied from the heat source 310 to the welding instrument 306, by way of example.

On the other hand, the reference values 338A and 338B potentially could be a part of a pre-existing specification for the weld that is being formed on the workpiece as part of the welding operation. Such a pre-existing specification of the weld might include, for instance, a target current value, a tolerance from that target current value, specifications for voltages, delivery pressure of inert gas, wire feed rate, and the like without limitation, and by way of example. Such a pre-existing specification of the weld might have been entered into the welding apparatus 304 by the worker 28 or may have been otherwise received thereon. In such a situation, by providing the current indicium 330A that indicates not only the current that is being provided to the welding instrument 306 but also indicates the current level in relation to the pair of tolerance reference values 338A and 338B, the worker 28 can be apprised of the fact that the current level may be approaching an upper limit or a lower limit as specified by the pre-existing specification. More specifically, the worker 28 is apprised of this fact prior to the current level meeting or exceeding the specified current limits. This advantageously enables the worker 28 to correct any shortcomings with the operation prior to the operation going outside the pre-established specification for the welding operation. This advantageously avoids the need to have the weld cut out and reformed. The avoidance of such reworking is advantageous.

One additional aspect of the disclosed and claimed concept is simply streaming a video of a data screen of the welding apparatus 304 to the worker 28, which could likewise be communicated wirelessly to the glasses 20 and visually output thereon. This would have the same effect as sending a digital signal from a sensor on the welding apparatus 304 to the glasses 20 for display. For instance, a camera could be positioned in proximity to the data screen on the heat source 310 and would capture video of the various analog or digital outputs on the data screen, which video would be visually output on the glasses 20. Other variations will be apparent.

The various other visual indicia 330B-G are depicted in FIG. 7A as being output in a numeric fashion, but it is understood that such visual indicia can additionally or alternatively or both be output in an analog fashion, such as with a needle like that employed by the current indicium 330A, or otherwise, to provide a visual analog output of the current.

Further advantageously, the worker 28 (or another individual) can select the specific way in which the various visual indicia 330 are output on the glasses 20, and the visual display 326 of FIG. 7A is merely one example of one way in which the visual indicia 330 can be visually output. For instance, the computer 316 includes a graphics engine 331 that interfaces with the glasses 20 and that enables the worker 28 to specify which parameters are to be output as visual indicia 330 on the glasses 20, the location of such visual indicia, and the specific format (e.g., numeric or any of a variety of analog depictions) in which each such visual indicium is to be depicted.

By way of example, FIG. 7B depicts another exemplary visual display 426 that can be visually output on the glasses 20 if selected by the worker 28. It is noted that the visual display 426 includes a number of visual indicia 430, some of which are visually different in some way than the visual indicia 330, but that visually output the same intellectual content as the visual indicia 330. Furthermore, while the exemplary parameters that are visually output as the visual indicia 330 are the same as those output as the visual indicia 430 in the visual display 426, it is understood that the worker 28 can decide which parameters to output on the glasses 20. Thus, the visual displays 326 and 426 might each include one or more visual indicia 330 and 430, respectively, that indicate parameters that are not shown in the other and that may include parameters different than or additional to or both than those depicted in the visual displays 326 and 426. Again, the worker 28 is able to customize the visual display that is provided on the glasses 20 to suit the needs of the worker 28 and the operation.

As can further be seen in FIG. 7B, the visual indicia 430 include a current indicium 430, a voltage indicium 430B, a feed rate indicium 430C, a fluid flow indicium 430D, a tank pressure indicium 430E, a delivery pressure indicium 430F, and a tank fullness indicium 430G, which may be collectively or individually referred to herein within the numeral 430 and which are in some ways similar to the visual indicia 330B-G in FIG. 7A. That is, all of the visual indicia 330B-G and the corresponding visual indicia 430B-G are all of a numeric nature, and some are situated at different positions on the visual displays 326 and 426. As suggested above, any of the aforementioned visual indicia 330 and 430 could instead be depicted in an analog fashion or could be absent and/or could be replaced with other visual indicia representative of other parameters, and could also be positioned elsewhere on the visual displays 326 and 426 depending upon the output format that is selected by the worker 28.

In the depicted exemplary embodiment, the current indicium 430A includes an indicator 434 that is depicted as being a dot from which a trace line 436 emanates as a function of time to the right of the indicator 434. The exemplary indicator 434 and trace line 436 thus operate as a control chart, examples of which include a needle mark traced onto a moving sheet of paper or an ECG trace, by way of example. The current indicium 430 includes a pair of reference values 438A and 438B that include both graduation marks and corresponding numeric calibration values situated below and above the indicator 434. The exemplary current indicium 430A further includes a pair of threshold values 440A and 440B that are indicated with dashed-line graduation marks and that represent threshold values that would have been input as part of a pre-existing specification for the weld that is being formed by the welding apparatus 304. The threshold values 440A and 440B are greater than the minimum value and less than the maximum value, respectively, of current as set forth in the pre-established specification of the weld and would be met prior to meeting the lower and upper current limits of "100" and "110", respectively, from the specification.

In this regard, another optional output that can be provided by the computer 316 is a set of notifications that are additional to the current indicium 430A, by way of example. For instance, depending upon the options selected by the worker 28, the computer 316 can output a first notification when the current value meets one of the threshold values 440A or 440B, and can output a second, different notification when either of the minimum or maximum current values "100" and "110", respectively, is reached, and can output a third notification in the event that the minimum or maximum current value is exceeded. Such notifications can be audible or visual or both or can take another form altogether without departing from the spirit of the instant disclosure. Any of a wide variety of visual and/or audible and/or other types of notifications can be envisioned.

Figure 7C:
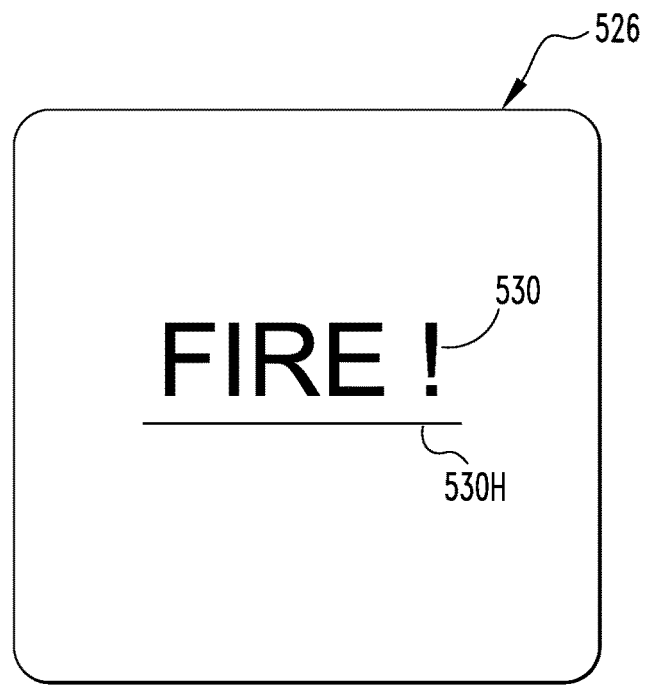

Another visual display 526 including visual indicia 530 in the form of a single fire warning indicium 530H is depicted in FIG. 7C. The fire warning indicium 530H is a textual spelling of the word "FIRE!" that is depicted on the glasses 20 and which takes the place of all other visual indicia on the visual display 526 in the depicted exemplary embodiment. This is intended to immediately gain the attention of the worker 28 due to such a potentially dangerous condition. It is understood that the fire warning indicium 530H is based upon a detection by the optical thermographic sensor 312J of the presence of a fire, and it is understood that the fire warning indicium 530H could itself take other forms such as employing graphical objects, color, and the like, and may be accompanied by audible and other notifications, and it potentially may additionally be accompanied by notifications that are sent electronically to the system 4 for communication to supervisors and the like.

Figure 7D:
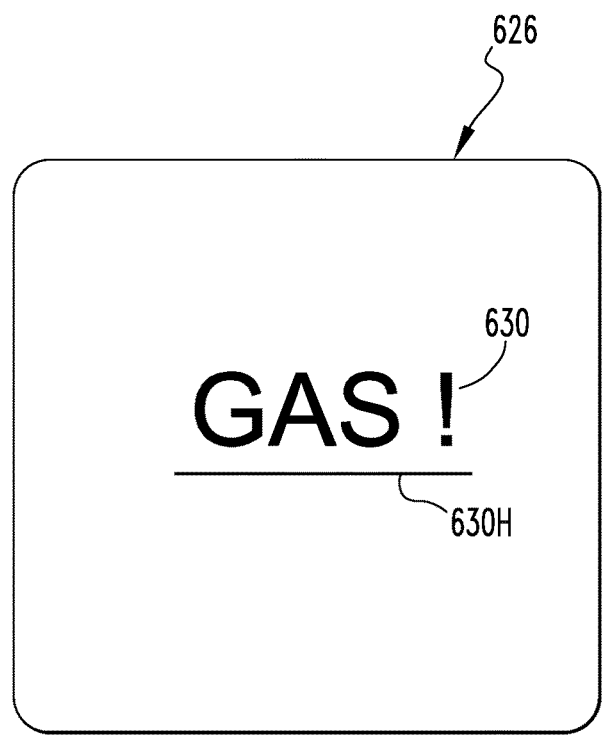

In a like fashion, another exemplary visual display 626 is depicted in FIG. 7D as having visual indicia 630 in the form of a single gas warning indicium 630H in the form of the textual word "GAS!" that is depicted on the glasses 20. Again, the visual display 626 includes only the gas warning indicium 630H in order to rapidly gain the attention of the worker 28. As before, the gas warning indicium 630H may be visually different than that pictured in FIG. 7 and may be accompanied by audible or other notifications and other actions being taken to alert management. It is understood that the gas warning indicium 630H in FIG. 7D could indicate any one or more of the existence of increased oxygen, decreased oxygen, and carbon monoxide, and it additionally could refer to any other gas whose presence has been detected by one of the detectors 312, depending upon the configuration of the welding apparatus 304. By way of example, the gas warning indicium 630H could alternatively be "INCREASED GAS!" or "CARBON MONOXIDE GAS!", by way of example. Other types of visual indicia will be apparent.

Figure 8:
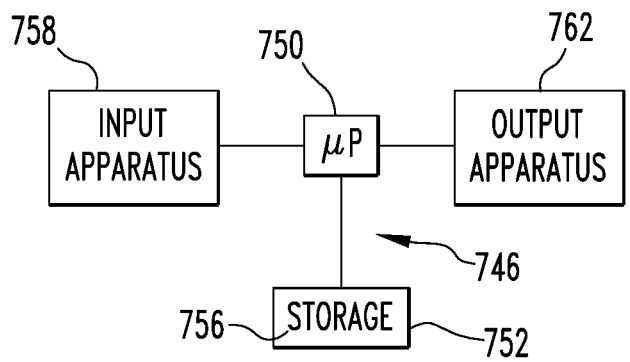
FIG. 8 is a schematic depiction of a computer of the welding apparatus of FIG. 6.

As can be understood from FIG. 8, the computer 316 can be said to include a processor apparatus 746 having a processor 750 and a storage 752 that are connected with one another. The processor 750 can be any of a wide variety of processors, such as a microprocessor, by way of example, and the storage 752 can be any one or more of RAM, ROM, EPROM, FLASH, and the like by way of example and without limitation, and which serves as storage area on the computer 316. The storage 752 has stored therein a number of routines 756 that include instructions which, when executed on the processor 750, cause the computer 316 and the welding apparatus 304 and the glasses 20 to perform certain operations. In this regard, it is understood that the glasses 20 may be considered to be a part of the welding apparatus 304.

The computer 316 further includes an input apparatus 758 that is connected with the processor 750 and which provides input signals to the processor apparatus 746. The input apparatus 758 is connected with the detectors 312 and can include other input sources such as a keypad, a mouse, a microphone for voice-based commands, and the like by way of example and without limitation. The pre-established specification for the weld operation can be entered via the input apparatus 758.

The computer 316 further includes an output apparatus 762 that is connected with the processor 750 and that receives output signals from the processor apparatus 746. In the depicted exemplary embodiment, the output apparatus 762 can include a wireless transceiver that is wirelessly connected with the glasses 20 in order to provide visual output on the glasses 20. The output apparatus 762 can additionally be connected with a loudspeaker that may be situated in proximity to an ear of the worker 28 or can be otherwise situated. The output apparatus 762 can additionally be connected with an input to the system 4 which can provide warning notifications pertaining to the existence of fire or other gas irregularity within the environment 303. Other examples will be apparent.

Figure 9:
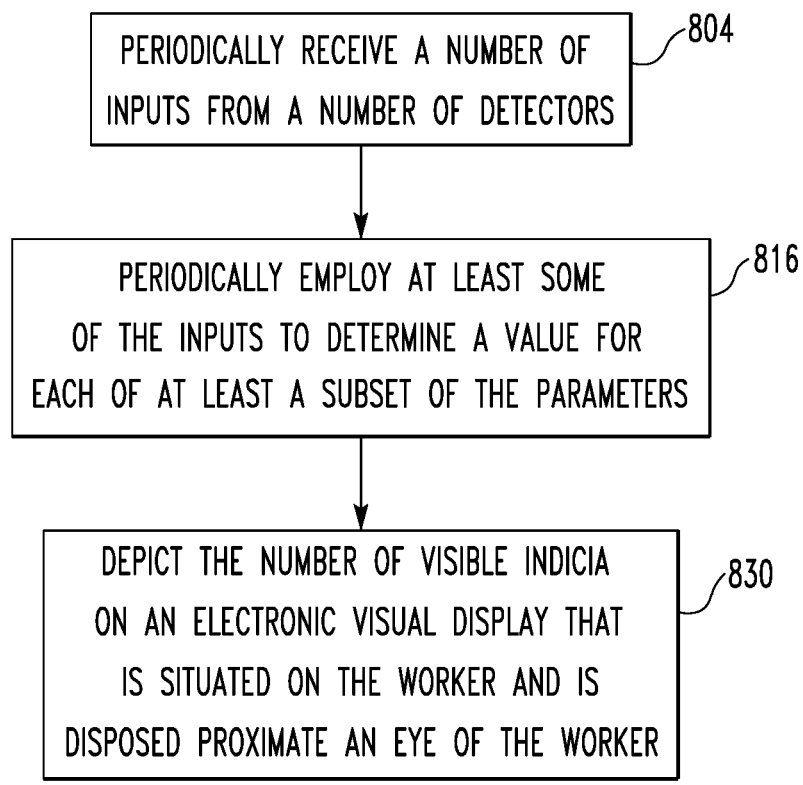
FIG. 9 is a flowchart depicting certain aspects of the improved method.

FIG. 9 depicts a flowchart that indicates aspects of an improved method in accordance with the disclosed and claimed concept. Processing can be said to begin, as at 804, where the computer 316 periodically receives from the detectors 312 a number of inputs that are representative of the properties of the welding apparatus 304 and the environment 303. Processing then continues, as at 716, where the computer 316 periodically employs at least some of the inputs from the detectors 312 to determine a value for at least a subset of the parameters, which could include one or more operational parameters of the welding apparatus 304 or one or more environmental parameters of the environment 303 or both. Processing then continues, as at 830, where the computer 316 and, more particularly, the graphics engine 331 thereof, depicts on the glasses 20 a number of visual indicia, such as the visual indicia 330, 430, 530, 630, etc., on an electronic visual display of the glasses 20 that is situated on the worker 28 and that is disposed proximate an eye of the worker 28. As noted elsewhere herein, the glasses 20 include an electronic visual display that is at least partially translucent, and thus the worker 28 can see not only the light rays from the environment 303 shining through the glasses 20, but the worker 28 can additionally visually perceive the visual indicia 330, 430, 530, 630, etc. Other variations will be apparent.

Advantageously, therefore, the welding apparatus 304 is configured to output on the glasses 20 a number of visual indicia that are representative of the values of one or more of the parameters of the welding apparatus 304 and the environment 303, as selected by the worker 28. The visual indicia are continually updated to reflect continually updated values for the parameters, which are based upon the periodically-received inputs from the detectors 312. The visual indicia provide to the worker 28 information regarding the values of the operational parameters of the welding apparatus 304 and the environmental parameters of the environment 303 to keep the worker 28 informed about the progress of the operation and the environment 303 in which the operation is being conducted. Such visual indicia can advise the worker that the operation potentially is about to meet or exceed a pre-established specification of the welding operation or other operation or a pre-established threshold thereof prior to the operation actually reaches or exceeds one of the pre-established limits of the pre-established specification or a threshold thereof. This advantageously avoids reworking and the like. Moreover, the ability of the welding apparatus 304 to output warnings to the worker with regard to dangers in the environment 303 additionally provides a beneficial measure of safety, which is desirable. Other benefits will be apparent.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A method of visually outputting to a worker during the performance of an operation that is being performed at least in part by the worker a number of visible indicia that are continually updated and that are representative of a number of parameters that pertain to the operation, the method comprising:
   periodically receiving a number of inputs from a number of detectors;
   periodically employing at least some of the inputs of the number of inputs to determine a value for each of at least a subset of parameters of the number of parameters; and
   depicting the number of visible indicia on an electronic visual display that is situated on the worker and is disposed proximate an eye of the worker, the number of visible indicia being representative of the value that corresponds with each parameter of at least some of the parameters of the at least subset.

2. The method of claim 1 wherein the electronic visual display is at least partially translucent, and wherein the depicting of the number of visible indicia comprises depicting the number of visible indicia on the at least partially translucent electronic visual display.

3. The method of claim 1 wherein the depicting of the number of visible indicia comprises depicting at least a subset of the number of visible indicia as being one of a numerical representation of at least a first value and an analog representation of at least a first value depicted as being positioned on the electronic visual display in relation to at least a first reference value.

4. The method of claim 3 wherein the number of parameters that pertain to the operation comprise a number of operational parameters that are related to the operation itself and a number of environmental parameters that are related to the environment in which the operation is being performed, and wherein the depicting of the at least subset of the number of visible indicia comprises depicting a representation of a corresponding value of each of at least a subset of the number of operational parameters.

5. The method of claim 4, further comprising visually outputting an alarm based at least in part on at least some of the environmental parameters of the number of environmental parameters.

6. The method of claim 5 wherein the number of environmental parameters comprise an amount of atmospheric oxygen in the environment in which the operation is being performed, and wherein the periodically receiving of the number of inputs from the number of detectors comprises periodically receiving from an oxygen detector of the number of detectors an input that is representative of an existence of one of increased atmospheric oxygen and decreased atmospheric oxygen in the environment in which the operation is being performed.

7. The method of claim 5 wherein the number of environmental parameters comprise an existence of carbon monoxide in the environment in which the operation is being performed, and wherein the periodically receiving of the number of inputs from the number of detectors comprises periodically receiving from a carbon monoxide detector of the number of detectors an input that is representative of an existence of carbon monoxide in the environment in which the operation is being performed.

8. The method of claim 5 wherein the number of environmental parameters comprise an existence of fire in the environment in which the operation is being performed, and wherein the periodically receiving of the number of inputs from the number of detectors comprises periodically receiving from a fire detector of the number of detectors an input that is representative of one of an existence of fire and an absence of fire in the environment in which the operation is being performed.

9. The method of claim 3 wherein the operation is a welding operation, and wherein a parameter of the number of parameters is one of a voltage and a current.

10. The method of claim 3 wherein the at least first reference value is based at least in part upon a pre-established specification for the welding operation.

11. The method of claim 10 further comprising receiving at least a portion of the pre-established specification as an input.

12. The method of claim 10 further comprising outputting a notification when the value of the parameter is within a predetermined threshold of the at least first reference value.

13. The method of claim 12 further comprising outputting another notification when the value of the parameter is equal to the at least first reference value.

14. The method of claim 13 further comprising outputting a further notification when the value of the parameter exceeds the at least first reference value.

15. The method of claim 3 further comprising receiving an input that is representative of a preferred style of visual output from among a plurality of available styles of visual output and, responsive thereto, depicting the number of visible indicia according to the preferred style.

16. The method of claim 1 wherein the operation is a welding operation, and wherein a parameter of the number of parameters is a wire feed rate.

17. The method of claim 1 wherein the operation is a welding operation, and wherein a parameter of the number of parameters is at least one of a fluid pressure and a fluid flow rate.

18. A welding apparatus structured to be usable by a worker to perform a welding operation, the welding apparatus comprising:
   a welding instrument structured to be manually held by the worker;
   a heat source connected with the welding instrument;
   a number of detectors, each detector of the number of detectors being structured to detect a property of at least one of the welding instrument, the heat source, and an environment in which the welding apparatus is situated;
   a processor apparatus connected with the number of instruments and comprising a processor and a storage;
   an electronic visual display that is structured to be situated on the worker and to be disposed proximate an eye of the worker, the electronic visual display being structured to visually output to the worker during the performance of the operation a number of visible indicia that are continually updated and that are representative of a number of parameters that pertain to the operation; and the storage having stored therein a number of routines which, when executed on the processor, cause the processor apparatus to perform a number of operations that comprise:

periodically receiving a number of inputs from the number of detectors;

periodically employing at least some of the inputs of the number of inputs to determine a value for each of at least a subset of parameters of the number of parameters; and depicting the number of visible indicia on the electronic visual display.

19. The welding apparatus of claim 18 wherein the electronic visual display is at least partially translucent, and wherein the depicting of the number of visible indicia comprises depicting the number of visible indicia on the at least partially translucent electronic visual display.

* * * * *